(12) United States Patent
Nagasaki et al.

(10) Patent No.: US 12,396,710 B2
(45) Date of Patent: Aug. 26, 2025

(54) ULTRASONIC DIAGNOSTIC APPARATUS AND ULTRASONIC PROBE

(71) Applicant: CANON MEDICAL SYSTEMS CORPORATION, Otawara (JP)

(72) Inventors: Yuya Nagasaki, Nasushiobara (JP); Yasuhisa Makita, Nasushiobara (JP); Masaaki Sudo, Yokohama (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 84 days.

(21) Appl. No.: 18/446,046

(22) Filed: Aug. 8, 2023

(65) Prior Publication Data

US 2024/0050075 A1  Feb. 15, 2024

(30) Foreign Application Priority Data

Aug. 9, 2022 (JP) .................. 2022-127414

(51) Int. Cl.
*A61B 8/00* (2006.01)

(52) U.S. Cl.
CPC ........ *A61B 8/56* (2013.01); *A61B 2560/0214* (2013.01); *A61B 2560/0266* (2013.01)

(58) Field of Classification Search
CPC .............. A61B 8/56; A61B 2560/0214; A61B 2560/0266; A61B 8/546
See application file for complete search history.

(56) References Cited

FOREIGN PATENT DOCUMENTS

| CN | 113040820 A | * | 6/2021 |
|---|---|---|---|
| JP | 2010-167083 A | | 8/2010 |
| JP | 2012179324 A | * | 9/2012 |
| JP | 2012228425 A | * | 11/2012 |

OTHER PUBLICATIONS

Oshima (JP 2012179324) machine translation (Year: 2012).*
Murakami (JP 2012228425) machine translation (Year: 2012).*
Du et al (CN 113040820) machine translation (Year: 2021).*

* cited by examiner

*Primary Examiner* — Alexei Bykhovski
(74) *Attorney, Agent, or Firm* — Oblon, McClelland, Maier & Neustadt, L.L.P.

(57) ABSTRACT

An ultrasonic diagnostic apparatus according to the present disclosure includes: an ultrasonic probe connected to an apparatus body, comprising a battery that supplies power to components of the ultrasonic probe and a cooler that cools inside the ultrasonic probe; and a drive controller that drives the cooler based on a remaining level of the battery and an internal temperature of the ultrasonic probe.

19 Claims, 9 Drawing Sheets

ULTRASONIC DIAGNOSTIC APPARATUS AND ULTRASONIC PROBE

CROSS REFERENCE TO RELATED APPLICATIONS

This application is based upon and claims the benefit of priority from the prior Japanese Patent Application No. 2022-127414, filed on Aug. 9, 2022, the entire contents of which are incorporated herein by reference.

FIELD

The embodiments disclosed in the present specification and drawings relate to an ultrasonic diagnostic apparatus and an ultrasonic probe.

BACKGROUND

In today's medical fields, ultrasonic diagnostic apparatuses are widely used to examine inside a subject by using ultrasonic waves generated with an ultrasonic probe. To examine inside the subject with the ultrasonic diagnostic apparatus, a subject contact of an ultrasonic probe having an ultrasonic transducer that transmits/receives ultrasonic waves should be brought into contact with the subject. For this reason, the international standard IEC60601-2-37 defines a temperature standard of the subject contact, and the temperature of the subject contact of the ultrasonic probe should be prevented from rising above a predetermined temperature.

Especially, in a wireless ultrasonic probe that connects an apparatus body with the ultrasonic probe of the ultrasonic diagnostic apparatus with wireless communication, a processing circuitry that performs signal processing etc. and a battery that supplies power to components of the ultrasonic probe are housed inside a housing case of the ultrasonic probe. Therefore, a usable time of the ultrasonic probe is limited by both a rising temperature of the ultrasonic probe due to heat generated by the processing circuitry etc. and a remaining level of the battery.

Here, the ultrasonic probe, in which the cooling unit is driven when an internal temperature exceeds a predetermined threshold, is proposed to suppress the rising temperature of the ultrasonic probe. Also proposed is the ultrasonic probe that shifts to a power savings mode when the remaining level of the battery falls below the predetermined threshold. However, with such ultrasonic probe, there is a concern of affecting the diagnosis using the ultrasonic diagnostic apparatus, since a performance of the ultrasonic probe may change regardless of an operator's intention. Moreover, there is a problem of being unable to secure a sufficient usable time of the ultrasonic probe, because the timing when the power of the battery depletes and the timing when the ultrasonic probe becomes unusable due to the rising temperature do not match.

DETAILED DESCRIPTION

With reference to the drawings below, embodiments of an ultrasonic diagnostic apparatus and an ultrasonic probe will be described. In the description below, note that same reference signs are given for components substantially identical in terms of configuration and function and duplicate description will be given only when necessary.

First Embodiment

Figure 1:
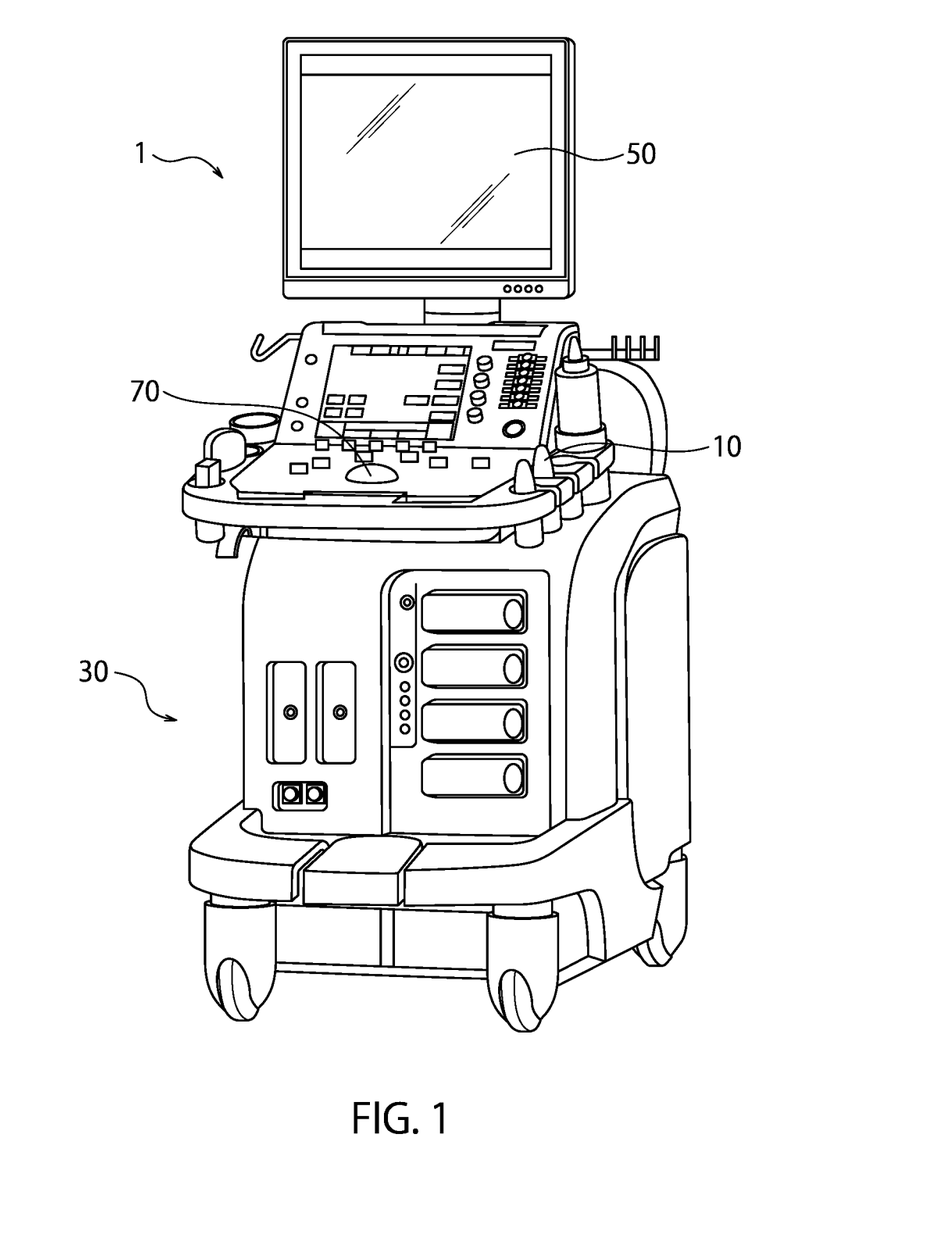
FIG. 1 is a perspective view schematically illustrating an exterior of the ultrasonic diagnostic apparatus according to a first embodiment.

FIG. 1 is a schematical diagram illustrating an exterior of the ultrasonic diagnostic apparatus according to a first embodiment. As shown in FIG. 1, the ultrasonic diagnostic apparatus 1 according to the present embodiment includes the ultrasonic probe 10, an apparatus body 30, a display 50, and an input interface 70. Note that in the example shown in FIG. 1, the display 50 and the input interface 70 are configured separately from the apparatus body 70, but the apparatus body 30, the display 50, and the input interface 70 may be configured as one. An example where the apparatus body 30, the display 50, and the input interface 70 are configured as one, for instance, includes an information processing device such as a tablet terminal or a workstation.

The ultrasonic probe 10 refers to a device connected to the apparatus body 30, which transmits an ultrasonic signal to a subject and receives a reflected wave signal based on the transmitted ultrasonic signal reflected within the subject. The ultrasonic probe 10, for instance, includes an 1D array probe which scans a 2-dimension area within the subject, or a mechanical 4D probe or a 2D array probe which scans a 3-dimension area within the subject. Although FIG. 1 illustrates an example where the ultrasonic probe 10 is connected to the apparatus body 30 with wireless communication, the ultrasonic probe 10 may be arranged to be connected to the apparatus body 30 with wired communication such as those via cables. Note that in the description below, the ultrasonic probe 10 according to the present embodiment will be described with an example where the ultrasonic probe 10 is arranged to be connected to the apparatus body 30 with wireless communication.

The apparatus body 30 refers to a device that generates ultrasonic images based on received signals received from the ultrasonic probe 10. In the example shown in FIG. 1, the ultrasonic probe 10, the display 50, and the input interface 70 are connected to the apparatus body 30 according to the present embodiment.

The display 50 refers to a display device that displays various ultrasonic images or various settings etc. For instance, the display 50 may display ultrasonic images generated by the apparatus body 30 or various settings performed by an operator. In the present embodiment, the display 50, for instance, is configured by a liquid crystal display or a Cathode Ray Tube (CRT) display etc. If the display 50 is configured by a display device that allows operation and input, the display 50 also displays a Graphical User Interface (GUI) etc., to receive various operations from the operator.

The input interface 70 refers to an input device to perform various settings etc., and is realized by, for instance, a trackball, a switch button, a mouse, a keyboard, a touchpad that performs input operations by touching an operating screen, a touch monitor where a display screen is combined with the touchpad, a non-touch input circuitry using a photosensor, or an audio input circuitry, etc. The input interface 70 connected to the processing circuitry of the apparatus body 30 which will be described later, converts the input operation received from the operator into electrical signal and outputs to the processing circuitry of the apparatus body 30. Note that the input interface 70 according to the present disclosure is not limited to those having physical components for operation such as the mouse or keyboard. For instance, the processing circuitry of the electrical signal that receives electrical signals corresponding to input operations from an external input device provided separately from the apparatus and outputs the electrical signal to the processing circuitry of the apparatus body 30, is also included as an example of the input interface 70.

Figure 2:
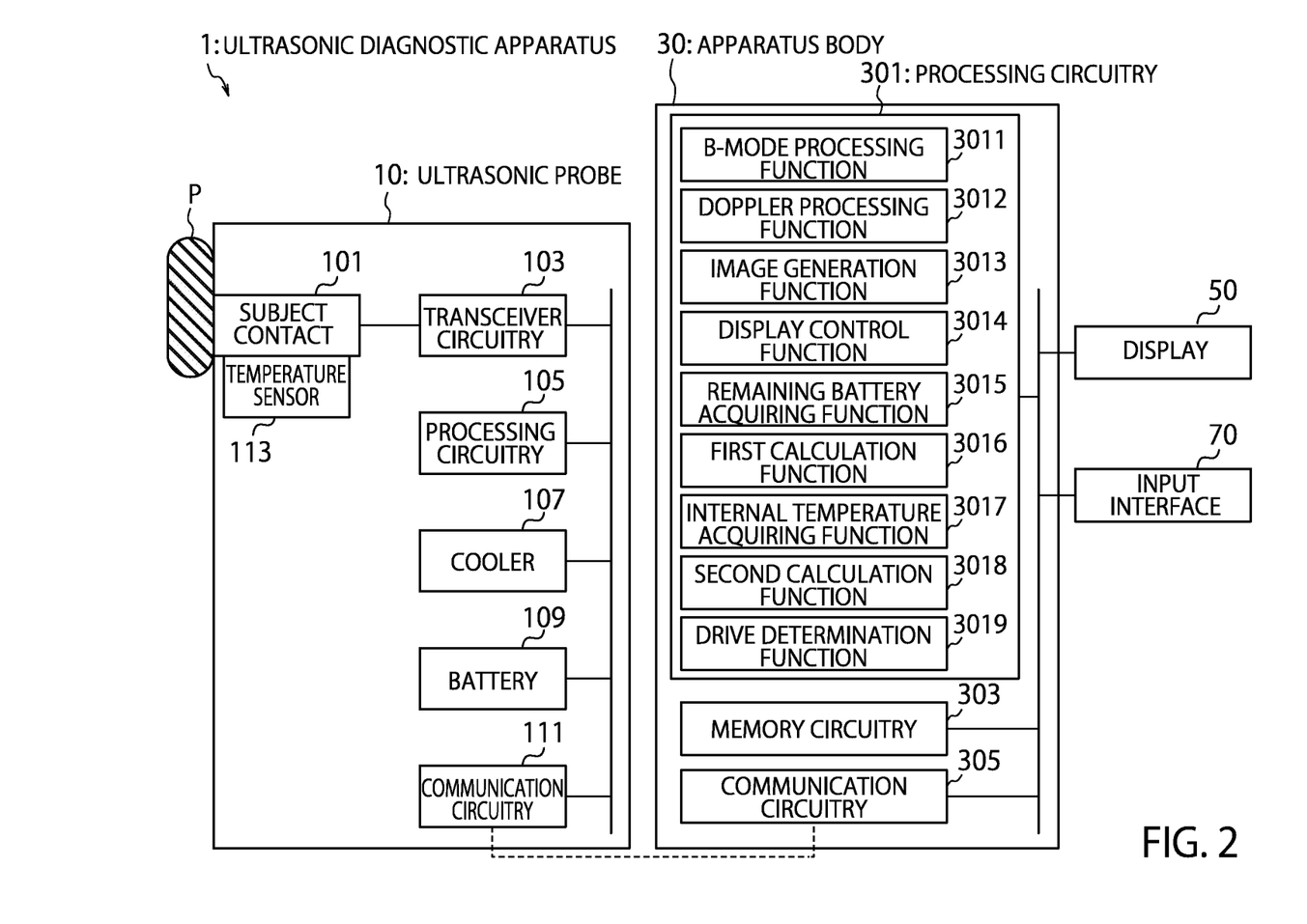
FIG. 2 is a block diagram illustrating an exemplary electrical configuration of the ultrasonic diagnostic apparatus according to the first embodiment.

Next, referring to FIG. 2, an exemplary configuration of the ultrasonic diagnostic apparatus 1 according to the present embodiment will be described. FIG. 2 is a block diagram illustrating an exemplary electrical configuration of the ultrasonic diagnostic apparatus 1 according to the first embodiment. As also described in FIG. 1, the ultrasonic diagnostic apparatus 1 according to the present embodiment shown in FIG. 2 includes the ultrasonic probe 10, the apparatus body 30, the display 50, and the input interface 70.

In further detail, the ultrasonic probe 10 which the ultrasonic diagnostic apparatus 1 according to the present embodiment includes, includes a subject contact 101, a transceiver circuitry 103, a processing circuitry 105, a cooler 107, a battery 109, a communication circuitry 111, and a temperature sensor 113. In the present embodiment, these components are stored in a single housing case. On the other hand, the apparatus body 30 which the ultrasonic diagnostic apparatus 1 according to the present embodiment includes, includes a processing circuitry 301, a memory circuitry 303, and a communication circuitry 305.

First, describing about the configuration of the ultrasonic probe 10, the subject contact 101, for instance, transmits ultrasonic waves to the subject P via a subject contact surface that contacts with the subject P on a transceiver side of the ultrasonic waves and receives the reflected waves of the transmitted ultrasonic waves reflected within subject P.

Thus, the subject contact 101 has an ultrasonic transducer that transmits/receives ultrasonic waves.

The ultrasonic transducer, for instance, refers to a piezoelectric oscillator made of piezoelectric ceramic. The ultrasonic transducer is provided as a plurality of arrays on a tip of the subject contact 101, transmits ultrasonic waves based on a drive signal supplied from the transceiver circuitry 103, receives reflected waves from inside of the subject P, and converts the reflected waves to electrical signals.

The transceiver circuitry 103 refers to a processor having a transmitter circuitry and a receiver circuitry that controls a transmission directivity and a receiving directivity in transmitting/receiving the ultrasonic waves. Note that in FIG. 2, an example was shown where the transceiver circuitry 103 is provided in the ultrasonic probe 10, but the transceiver circuitry 103 may be provided in both the ultrasonic probe 10 and the apparatus body 30.

The transmitter circuitry includes a pulse generator, a transmission delay circuitry, and a pulsar circuitry etc., and supplies the drive signal to the ultrasonic transducer. The pulse generator repeatedly generates a rate pulse to form the transmitting ultrasonic signal at a preset rate frequency. The transmission delay circuitry applies a delay time for every piezoelectric oscillation necessary to converge the ultrasonic wave generated from the ultrasonic transducer into a beam and determine the transmission directivity, to each rate pulse generated by the pulse generator. Further, the pulsar circuitry applies a drive pulse to the ultrasonic transducer at timings based on the rate pulse. The transmission delay circuitry arbitrarily adjusts a transmission direction of the ultrasonic wave transmitted from an ultrasonic transducer surface by modifying the delay time applied to each rate pulse.

The receiver circuitry includes an amplifier circuitry, A/D converter, an adder etc., receives reflected wave signals based on the reflected waves received by the ultrasonic transducer, and generates the received signal (echo signal) by performing various processing to the received wave signals. The amplifier circuitry amplifies reflected wave signals for each channel and performs gain correction processing. The A/D converter A/D converts the gain-corrected reflected wave signals and applies the delay time necessary to determine the receiving directivity to the digital data. The adder generates the received signals by performing an adding process of the reflected wave signals processed by the A/D converter. A reflective component from a direction in response to the receiving directivity of the reflected wave signals, is enhanced by the adding process of the adder.

The processing circuitry 105, for instance, refers to a control circuitry that performs an overall control of the ultrasonic probe 10, and for instance is configured by processors such as a CPU or GPU. The processing circuitry 105 according to the present embodiment controls the transceiver circuitry 103, the cooler 107, or the battery 109.

The cooler 107 refers to a cooling device that cools inside the ultrasonic probe 10. The cooler 107 may be configured by an air-cooling device using a fan etc., a liquid cooling device where a heat conducting fluid flows inside a pipe arranged within the ultrasonic probe 10, or an electrical cooling device such as a Piezo element or a Peltier element. In the present embodiment, the cooler 107 may turn its drive ON or OFF. Power is supplied from the battery 109 when driving the cooler 107. In other words, the remaining level of the battery 109 decreases by driving the cooler 107.

The battery 109 supplies power to each component of the ultrasonic probe 10. In the present embodiment, the battery 109 is configured by, for instance, rechargeable batteries such as lithium-ion batteries or nickel-metal hydride batteries. The battery 109, for instance, supplies power to the transceiver circuitry 103, the processing circuitry 105, the cooler 107, or the communication circuitry 111 etc. Note that the battery 109 may use non-rechargeable batteries as well as rechargeable batteries.

The communication circuitry 111 implements various protocols for wireless communications, realizing communication with the apparatus body 30 with wireless communication. The communication circuitry 111 according to the present embodiment, for instance, transmits the received signal generated by the receiver circuitry of the transceiver circuitry 103 to the apparatus body 30 with wireless communication. Note that in the example of FIG. 1 according to the present embodiment, the ultrasonic probe 10 and the apparatus body 30 communicates with wireless communication, but the communication between the ultrasonic probe 10 and the apparatus body 30 is not limited to wireless communication. For instance, if the communication between the ultrasonic probe 10 and the apparatus body 30 is done with wired communication, the communication circuitry 111 may implement various protocols for wired communication, realizing communication between the ultrasonic probe 10 and the apparatus body 30 with wired communication via such as cables.

The temperature sensor 113 refers to a sensor that detects an internal temperature of the ultrasonic probe 10. The temperature sensor 113 may be configured by, for instance, sensors such as a thermocouple, a resistance temperature detector, a thermistor, or an IC temperature sensor. Especially in the present embodiment, the temperature sensor 113 detects the temperature of the subject contact 101 or its vicinity, and outputs the detected temperature to the processing circuitry 105 as the internal temperature of the ultrasonic probe 10.

Figure 3:
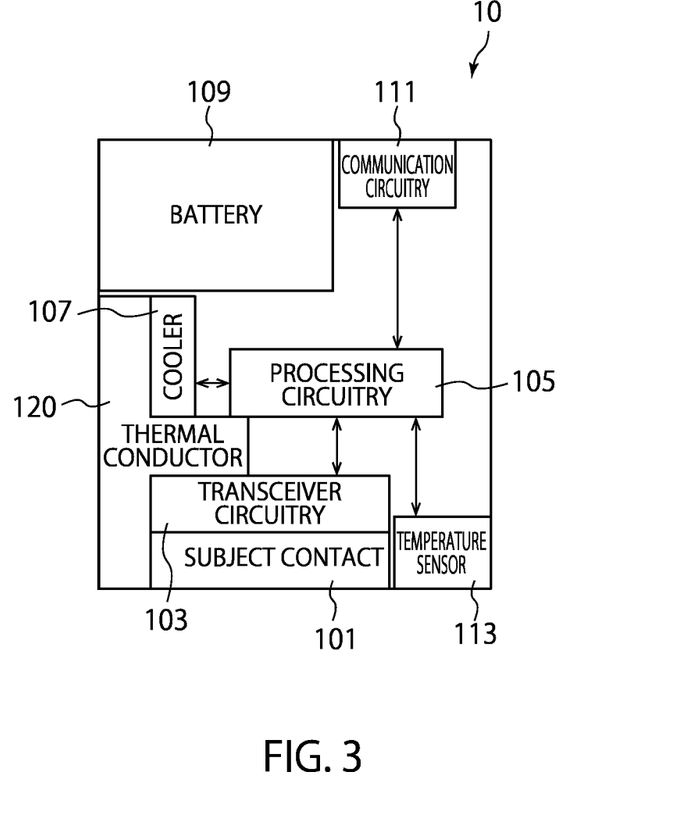
FIG. 3 is a description diagram describing an exemplary internal layout of the ultrasonic diagnostic apparatus according to the first embodiment.

FIG. 3 is a diagram that describes an exemplary internal layout of the ultrasonic probe 10 which the ultrasonic diagnostic apparatus 1 according to the present embodiment includes. As shown in FIG. 3, the ultrasonic probe 10 according to the present embodiment includes a thermal conductor 120. The thermal conductor 120, for instance, is configured by heat transfer members consisting of graphite or metals with high thermal conductivity such as aluminum or copper. Also, the thermal conductor 120 is arranged to be cooled by the cooler 107.

In the present embodiment, the thermal conductor 120 connects the subject contact 101 and the battery 109 so that heat may be transferred to each other between at least the subject contact 101 and the battery 109. By this, the subject contact 101 and the battery 109 may be efficiently cooled to suppress the temperature rise of these.

Likewise, the thermal conductor 120 may be formed and arranged so that heat is also transferred to each other between the transceiver circuitry 130, the processing circuitry 105, and the communication circuitry 111, in addition to the subject contact 101 and the battery 109. By this, the transceiver circuitry 103, the processing circuitry 105, and the communication circuitry 111 may also be efficiently cooled by the cooler 107.

Returning to FIG. 2 again, the processing circuitry 301, the memory circuitry 303, and the communication circuitry 305 that configures the apparatus body 30 will be described.

The processing circuitry 301 refers to a control circuitry that performs an overall control of the ultrasonic diagnostic apparatus 1. Likewise, the processing circuitry 301 also refers to an arithmetic circuitry that performs various calculations, and for instance, is configured by processors such as CPU or GPU. The processing circuitry 301 according to the present embodiment, for instance, generates ultrasonic image data based on received signals via the communication circuitry 305 or displays the generated ultrasonic image data on the display 50.

Thus, the processing circuitry 301 according to the present embodiment has a B-mode processing function 3011, a Doppler processing function 3012, an image generation function 3013, a display control function 3014, a remaining battery acquiring function 3015, a first calculation function 3016, an internal temperature acquiring function 3017, a second calculation function 3018, and a drive determination function 3019. The B-mode processing function 3011 is equivalent to a B-mode processor according to the present embodiment; the Doppler processing function 3012 is equivalent to a Doppler processor according to the present embodiment; the image generation function 3013 is equivalent to an image generator according to the present embodiment; and the display control function 3014 is equivalent to a display controller according to the present embodiment. Also, the remaining battery acquiring function 3015 is equivalent to a remaining battery acquirer according to the present embodiment; the first calculation function 3016 is equivalent to a first calculator according to the present embodiment; the internal temperature acquiring function 3017 is equivalent to an internal temperature acquirer according to the present embodiment; the second calculation function 3018 is equivalent to a second calculator according to the present embodiment; and the drive determination function 3019 is equivalent to a drive determiner according to the present embodiment. Also, the processing circuitry 301 is equivalent to a drive controller according to the present embodiment.

In the embodiment shown in FIG. 2, each processing function performed in the B-mode processing function 3011, the Doppler processing function 3012, the image generation function 3013, the display control function 3014, the remaining battery acquiring function 3015, the first calculation function 3016, the internal temperature acquiring function 3017, the second calculation function 3018, and the drive determination function 3019 is stored in the memory circuitry 303 in a form of computer executable program. The processing function 301 refers to a processor that realizes functions corresponding to each program by reading and executing the program from the memory circuitry 303. In other words, the processing circuitry 301 that has read each program has each function shown in the processing circuitry 301 in FIG. 2. Note that it was described in FIG. 2 to realize the B-mode processing function 3011, the Doppler processing function 3012, the image generation function 3013, the display control function 3014, the remaining battery acquiring function 3015, the first calculation function 3016, the internal temperature acquiring function 3017, the second calculation function 3018, and the drive determination function 3019 with a single processing circuitry 301, but these functions may be realized by combining a plurality of independent processors to arrange the processing circuitry 301 and let each processor execute the program.

The B-mode processing function 3011 refers to a function that generates B-mode data based on received signals received from the ultrasonic probe 10. The processing circuitry 301 performs, for instance, an envelope detection or a logarithmic compression to the received signal from the ultrasonic probe 10 with the B-mode processing function 3011 and generates B-mode data where a signal intensity is represented by brightness of luminosity.

The Doppler processing function 3012 refers to a function that generates Doppler data such as a blood flow velocity, a blood flow dispersion, or a blood flow power based on received signals received from the ultrasonic probe 10. The Doppler processing function 3012 generates Doppler data which extracts blood flow information based on a Doppler effect of a moving body within a region of interest (ROI) set to a scanning region by frequency analyzing the received signals received from the ultrasonic probe 10.

The image generation function 3013 refers to a function that generates the ultrasonic image data based on received signals received from the ultrasonic probe 10. Specifically, the image generation function 3013 refers to a function that generates various ultrasonic image data based on B-mode data generated by the B-mode processing function 3011 and/or Doppler data generated by the Doppler processing function 3012. For instance, the image generation function 3013 generates a B-mode image data representing the intensity of the reflected waves as luminance, from the B-mode data generated by the B-mode processing function 3011. Also, for instance, the image generation function 3013 generates an average velocity image, a dispersion image, a power image, or a combined image of these as a Doppler image data, from the Doppler data generated by the Doppler processing function 3012.

The display control function 3014 refers to a function that displays various ultrasonic image data generated by the image generation function 3013 on the display 50. Specifically, for instance, the display control function 3014 controls the display of the B-mode image data, the Doppler image data, or the ultrasonic image data including both, generated by the image generation function 3013, on the display 50.

The remaining battery acquiring function 3015 acquires the remaining battery level of the ultrasonic probe 10. Specifically, the remaining battery acquiring function 3015 acquires the remaining level of the battery 109 via the communication circuitry 305 and the communication circuitry 111. In the present embodiment, for instance, the remaining level of the battery 109 may be managed in the battery 109 itself or be managed by the processing circuitry 105. Also, the remaining level of the battery 109, for instance, may be represented as a percentage of the remaining level at that time with a fully charged state as 100% and a fully discharged state as 0%.

Also, the remaining battery acquiring function 3015 records the acquired remaining level of the battery 109 over time as a detection result. The recording of the detection result over time may be held by the remaining battery acquiring function 3015 or stored and held in the memory circuitry 303.

The first calculation function 3016 calculates a first usable time, which is the remaining usage time of the ultrasonic probe 10 corresponding to the remaining level, based on the remaining level of the battery 109 acquired by the remaining battery acquiring function 3015.

The internal temperature acquiring function 3017 acquires the internal temperature of the ultrasonic probe 10. Specifically, the internal temperature 3017 acquires the internal temperature of the ultrasonic probe 10 via the communication circuitry 305 and the communication circuitry 111. As described above, the internal temperature of the ultrasonic probe 10 is regularly detected and output to the processing circuitry 105 by the temperature sensor 113. Thus, the internal temperature acquiring function 3017 acquires the temperature detected by the temperature sensor 113 as the internal temperature of the ultrasonic probe 10.

Also, the internal temperature acquiring function 3017 records the acquired internal temperature of the ultrasonic probe 10 as the detection result over time. The record of the detection result over time may be held by the internal temperature acquiring function 3017 or stored and held in the memory circuitry 303.

The second calculation function 3018 calculates a second usable time, which is the remaining usage time of the ultrasonic probe 10 corresponding to the internal temperature of the ultrasonic probe 10, based on the internal temperature acquired by the internal temperature acquiring function 3017.

The drive determination function 3019 determines whether to drive the cooler 107 based on the first usable time calculated by the first calculation function 3016 and the second usable time calculated by the second calculation function 3018. In other words, the drive determination function 3019 determines whether to drive an inactive cooler 107. Further, the drive determination function 3019 determines whether to stop the cooler 107 based on the first usable time calculated by the first calculation function 3016 and the second usable time calculated by the second calculation function 3018. In other words, the drive determination function 3019 determines whether to stop an active cooler 107.

The memory circuitry 303 may be realized by semiconductor elements such as a random access memory (RAM) or a flash memory etc., a hard disk, or an optical disk etc. In the present embodiment, for instance, the memory circuitry 303 stores the program executed in the circuitry included in the ultrasonic probe 10 or the apparatus body 30.

The communication circuitry 305 implements various protocols for telecommunication in response to a form of a network. The communication circuitry 305 realizes communication with other apparatus via the network following these various protocols. For instance, the communication circuitry 305 according to the present embodiment receives the received signals generated by the receiver circuitry of the transceiver circuitry 103 of the ultrasonic probe 10, transmits a control program of the ultrasonic probe 10 to the ultrasonic probe 10, or transmits ultrasonic images etc., generated by the apparatus body 30 to other devices. As described above, in the present embodiment, the communication circuitry 305 and the communication circuitry 111 communicates with wireless communication but may communicate with wired communication as well.

Figure 4:
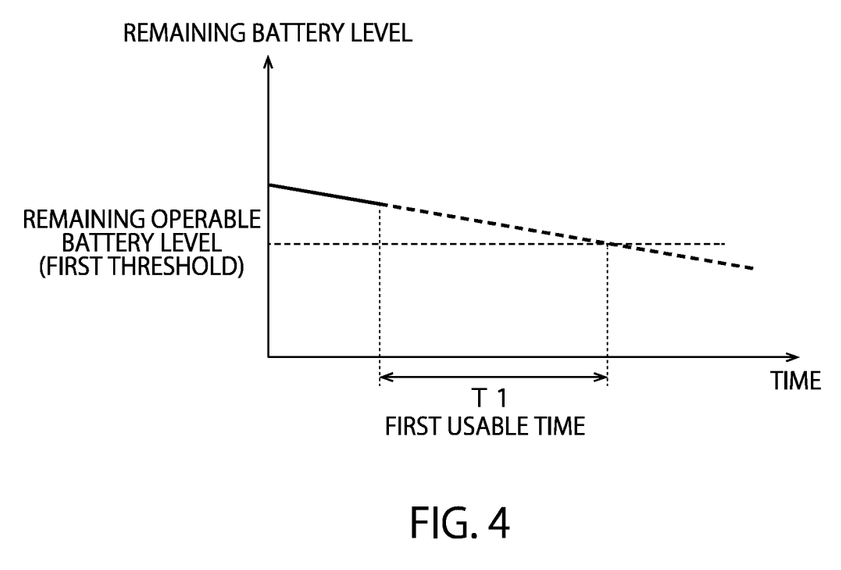
FIG. 4 is a diagram illustrating a graph showing a relationship between a remaining level of a battery of an ultrasonic probe and a usable time of the ultrasonic probe which the ultrasonic diagnostic apparatus according to the first embodiment includes.

FIG. 4 is a diagram illustrating a graph showing a relationship between the remaining level of the battery 109 of the ultrasonic probe 10 and the usable time of the ultrasonic probe 10 which the ultrasonic diagnostic apparatus 1 according to the present embodiment includes. Solid lines in FIG. 4 denote the detection result of the remaining level of the battery 109 so far. With a premise that this change continues, the remaining battery level is estimated to change from now on as shown with a dotted line. However, the ultrasonic probe 10 cannot be properly used when the remaining battery level falls below a first threshold, which is a predetermined remaining level. Thus, the first calculation function 3016 calculates the time until the remaining level of the battery 109 falls below the first threshold as the first usable time, which is the remaining usage time of the ultrasonic probe 10. In other words, the first usable time denotes the time from a current time T1 until the remaining level of the battery 109 falls below the first threshold.

Figure 5:
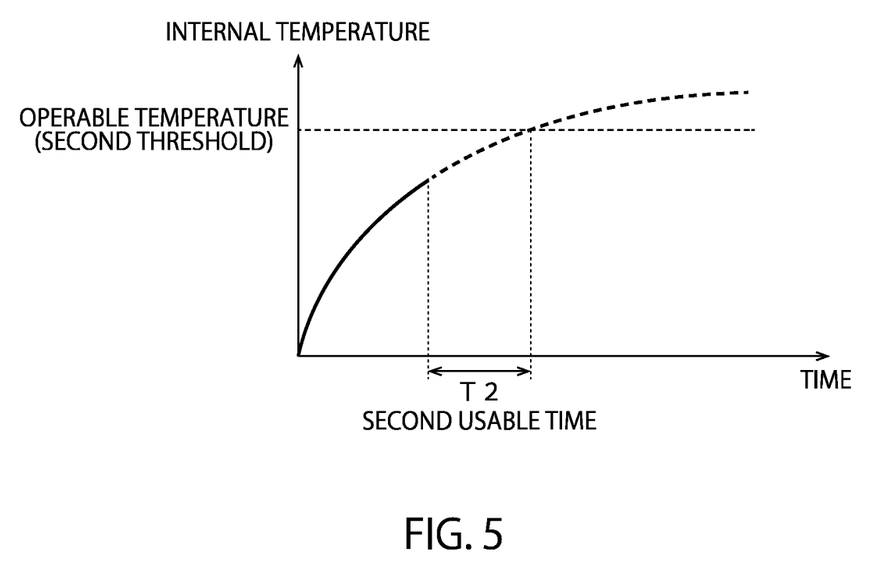
FIG. 5 is a diagram illustrating a graph showing a relationship between an internal temperature of the ultrasonic probe and the usable time of the ultrasonic probe which the ultrasonic diagnostic apparatus according to the first embodiment includes.

FIG. 5 is a diagram illustrating a graph showing a relationship between the internal temperature of the ultrasonic probe 10 and the usable time of the ultrasonic probe 10 which the ultrasonic diagnostic apparatus 1 according to the present embodiment includes. The solid lines in FIG. 5 denotes the detection result of the internal temperature of the ultrasonic probe 10 until now. With the premise that this change continues, the internal temperature is estimated to change from now on as shown with the dotted line. However, considering effects to a patient, the ultrasonic probe 10 cannot be used when the internal temperature rises above a second threshold, which is a predetermined temperature. Thus, the second calculation function 3018 calculates the time until the internal temperature of the ultrasonic probe 10 rises above the second threshold as the second usable time, which is the remaining usage time of the ultrasonic probe 10. In other words, the second usable time denotes the time from a current time T2 until the internal temperature of the ultrasonic probe 10 rises above the second threshold.

Here, the second usable time which depends on the internal temperature of the ultrasonic probe 10 extends when the cooler 107 is driven to suppress the internal temperature rise of the ultrasonic probe 10. However, the power of the battery 109 will be consumed when the cooler 107 is driven. Thus, the first usable time depending on the remaining level of the battery 109 shortens. As such, the relationship between the first usable time and second usable time trade-offs.

Figure 6:
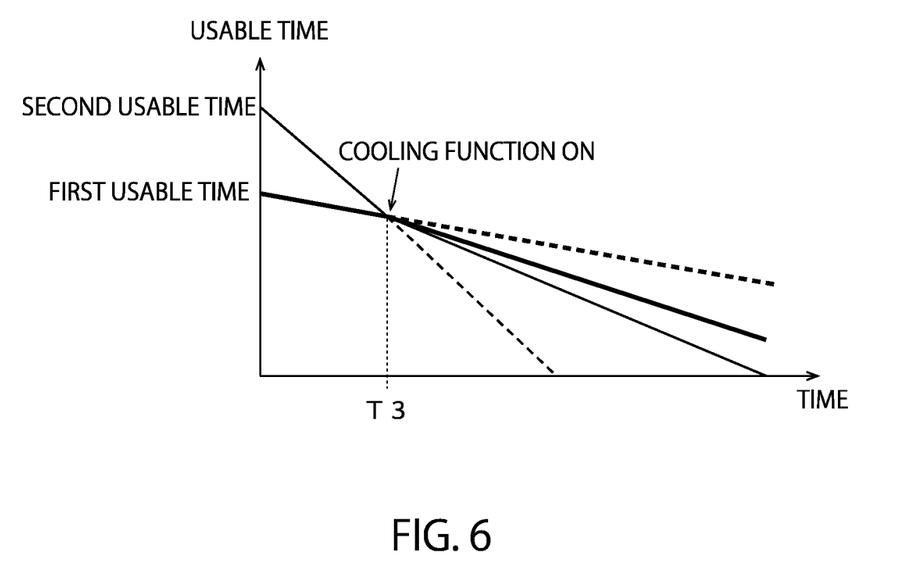
FIG. 6 is a diagram illustrating a graph showing a change of the usable time of the ultrasonic probe when a cooler is driven at some time.

FIG. 6 is a diagram illustrating a graph showing a change of the usable time of the ultrasonic probe 10 when the cooler 107 is driven at some time T3. In FIG. 6, a bold line represents the change of the first usable time, which is the remaining usage time based on the remaining level of the battery 109, and a thin line represents the change of the second usable time, which is the remaining usage time based on the internal temperature of the ultrasonic probe 10. In both the bold and thin lines, the solid line represents an estimate when driving the cooler 107 and an actual value, which is the detection result so far, and the dotted line represents an estimate when the cooler 107 was not driven.

As may be known from the change of the solid and dotted bold lines after time T3 in the graph of FIG. 6, an inclination of the solid line becomes steeper than that of the dotted line when the cooler 107 is driven, and the first usable time, which is the remaining usage time based on the remaining level of the battery 109, shortens since the power of the battery 109 is consumed. On the other hand, as may be known from the change of the solid and dotted lines related to the thin line after time T3 in the graph of FIG. 6, an inclination of the solid line becomes lenient than that of the dotted line when the cooler 107 is driven, and the second usable time, which is the remaining usage time based on the internal temperature of the ultrasonic probe 10, extends.

Here, to allow the operator to use the ultrasonic probe 10 as long as possible, it is preferable to have the difference between the first usable time, which is the remaining usage time based on the remaining level of the battery 109, and the second usable time, which is the remaining usage time based on the internal temperature of the ultrasonic probe 10, as small as possible. In other words, in the graph of FIG. 6, it is preferable to have the solid part of the bold line showing the first usable time and the solid part of the thin line showing the second usable time to match as possible.

There, in the ultrasonic diagnostic apparatus 1 according to the present embodiment, the drive of the cooler 107 is controlled based on the remaining level of the battery 109 and the internal temperature of the ultrasonic probe 10. Specifically, the drive of the cooler 107 is controlled based on the first usable time, which is the remaining usage time based on the remaining level of the battery 109, and the second usable time, which is the remaining usage time based on the internal temperature of the ultrasonic probe 10; and the difference between the first usable time, which is the remaining usage time corresponding to the remaining level of the battery 109, and the second usable time, which is the remaining usage time corresponding to the internal temperature of the ultrasonic probe 10, is made as small as possible.

Figure 7:
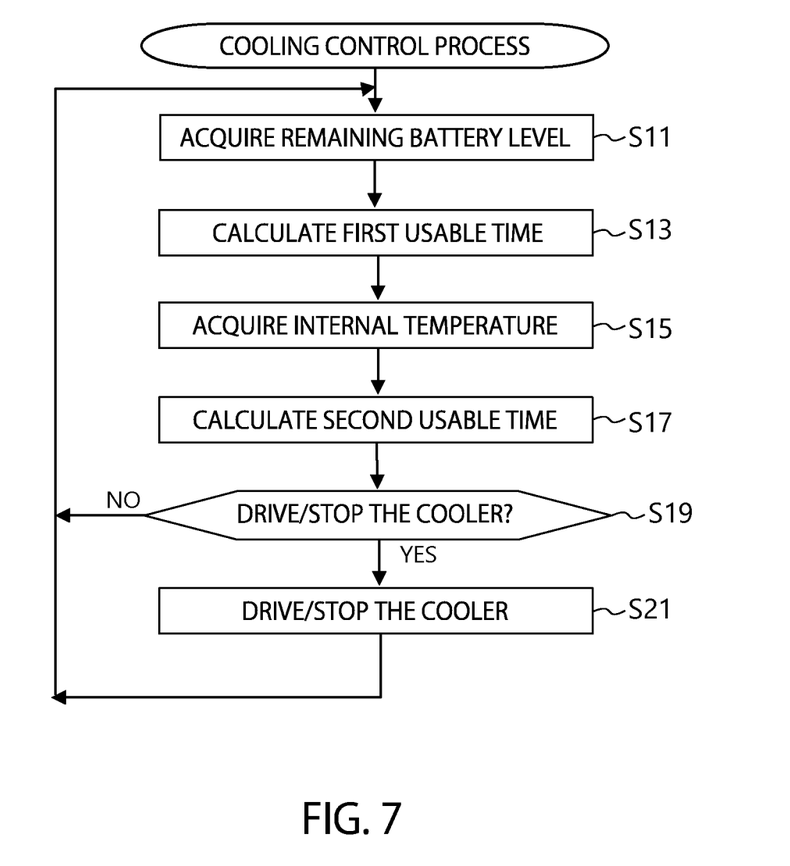
FIG. 7 is a diagram illustrating a flowchart describing contents of a cooling control process executed in the ultrasonic diagnostic apparatus according to the first embodiment.

To control the drive of the cooler 107 as such, the ultrasonic diagnostic apparatus 1 according to the present embodiment executes a cooling control process as shown in FIG. 7. In other words, FIG. 7 is a diagram illustrating a flowchart describing contents of the cooling control process executed in the ultrasonic diagnostic apparatus 1 according to the present embodiment. In the present embodiment, the cooling control process shown in FIG. 7, for instance, is executed in the processing circuitry 301 in the apparatus body 30 of the ultrasonic diagnostic apparatus 1. Likewise, the cooling control process refers to a process regularly executed when the ultrasonic diagnostic apparatus 1 is in operation.

As shown in FIG. 7, in the cooling control process, the ultrasonic diagnostic apparatus 1 first acquires the remaining level of the battery 109 (Step S11). Specifically, the remaining battery acquiring function 3015 in the processing circuitry 301 of the ultrasonic diagnostic apparatus 1 acquires the remaining level of the battery 109 from the ultrasonic probe 10 at that time.

Next, the ultrasonic diagnostic apparatus 1 calculates the first usable time, which is the remaining usage time of the ultrasonic probe 10 corresponding to the remaining level of the battery 109 based on the remaining level of the battery 109 acquired at Step S11 (Step S13). Specifically, the first calculation function 3016 in the processing circuitry 301 of the ultrasonic diagnostic apparatus 1 calculates the first usable time based on the remaining level of the battery 109 acquired by the remaining battery acquiring function 3015. The first calculation function 3016, for instance, as shown in FIG. 4, estimates the change of the remaining battery level thereafter from the detection result of the remaining level of the battery 109 so far and calculates the time until falling below the first threshold, which is the remaining operable battery level, as the first usable time.

Next, as shown in FIG. 7, the ultrasonic diagnostic apparatus 1 acquires the internal temperature of the ultrasonic probe 10 (Step S15). Specifically, the internal temperature acquiring function 3017 in the processing circuitry 301 of the ultrasonic diagnostic apparatus 1 acquires the internal temperature of the ultrasonic probe 10 at that time from the ultrasonic probe 10.

Next, the ultrasonic diagnostic apparatus 1 calculates the second usable time, which is the remaining usage corresponding to the internal temperature of the ultrasonic probe 10 based on the internal temperature of the ultrasonic probe 10 acquired at Step S15 (Step S17). Specifically, the second calculation function 3018 in the processing circuitry 301 of the ultrasonic diagnostic apparatus 1 calculates the second usable time based on the internal temperature of the ultrasonic probe 10 acquired by the internal temperature acquiring function 3017. The second calculation function 3018, for instance, as shown in FIG. 5, estimates the change of the internal temperature thereafter from the detection result of the internal temperature of the ultrasonic probe 10 so far and calculates the time until rising above the second threshold, which is an operable temperature, as the second usable time.

Next, as shown in FIG. 7, the ultrasonic diagnostic apparatus 1 determines whether to drive or stop the cooler 107 (Step S19). Specifically, the drive determination function 3019 in the processing circuitry 301 of the ultrasonic diagnostic apparatus 1 determines whether to drive the inactive cooler 107 or stop the active cooler 107 based on the first usable time calculated by the first calculation function 3016 and the second usable time calculated by the second calculation function 3018.

For instance, when the cooler 107 is inactive, the drive determination function 3019 determines to drive the cooler 107 when the first usable time, which is the remaining usage time corresponding to the remaining level of the battery 109, is longer than the second usable time, which is the remaining usage time corresponding to the internal temperature of the ultrasonic probe 10. By such, although the power of the battery 109 is used to drive the cooler 107, the internal temperature rise of the ultrasonic probe 10 is suppressed, decreasing the difference between the first usable time and the second usable time, and changing in a direction where the first usable time and the second usable time match.

On the other hand, when the cooler 107 is active, the drive determination function 3019 determines to stop the cooler 107 when the first usable time, which is the remaining usage time corresponding to the remaining level of the battery 109, is shorter than the second usable time, which is the remaining usage time corresponding to the internal temperature of the ultrasonic probe 10. By such, although the internal temperature rise of the ultrasonic probe 10 is not suppressed, the power of the battery 109 to drive the cooler 107 is not used, decreasing the difference between the first usable time and the second usable time and changing in a direction where the first usable time and the second usable time match.

When driving or stopping the cooler 107, the drive determination function 3019 may have a grace period when switching the drive and stop. For instance, when the drive determination function 3019 drives the cooler 107, the cooler 107 is continuously driven for 5 minutes thereafter. In contrast, when the drive determination function 3019 stops the cooler 107, the cooler 107 is not driven for 5 minutes thereafter. By such, it becomes possible to prevent the cooler 107 from repeating the drive and stop in a short period of time.

Next, as shown in FIG. 7, when determining to drive or stop the cooler 107 at Step S19 (Step S19: Yes), the ultrasonic diagnostic apparatus 1 drives the inactive cooler 107 or stops the active cooler 107 (Step S21). Specifically, the drive determination function 3019 in the processing circuitry 301 of the ultrasonic diagnostic apparatus 1 sends a command to the processing circuitry 105 of the ultrasonic probe 10 via the communication circuitry 305 and the communication circuitry 111, commanding to drive or stop the cooler 107.

After the drive determination function 3019 commands to drive or stop the cooler 107 at Step S21 and when the drive determination function 3019 determines that driving or stopping the cooler 107 is unnecessary at Step S19 described above (Step S19: No), the drive determination function 3019 returns to Step S11 described above and repeats the process from Step S11.

Note that the cooler 107 not only performs the simple control of drive and stop but also may adjust an intensity of a cooling function. For instance, the cooler 107 may have three levels (strong, medium, weak) as the intensity of the cooling function. In such case, the drive determination function 3019 may drive the cooler 107 with cooling functions of different intensity based on how great the difference between the first usable time and the second usable time is.

For instance, the difference between the first usable time, which is the remaining usage time corresponding to the remaining level of the battery 109, and the second usable time, which is the remaining usage time corresponding to the internal temperature of the ultrasonic probe 10, may be divided into three by a first difference and a second difference. Here, the second difference is greater than the first difference.

Then, if the first usable time, which is the remaining usage time corresponding to the remaining level of the battery 109, is longer than the second usable time, which is the remaining usage time corresponding to the internal temperature of the ultrasonic probe 10, and if the difference between the first usable time and the second usable time is less than the first difference, the drive determination function 3019 drives the cooler 107 with the cooling function of weak level.

On the other hand, if the first usable time, which is the remaining usage time corresponding to the remaining level of the battery 109, is longer than the second usable time, which is the remaining usage time corresponding to the internal temperature of the ultrasonic probe 10, and if the difference between the first usable time and the second usable time is greater than or equal to the first difference and less than the second difference, the drive determination function 3019 drives the cooler 107 with the cooling function of medium level.

Further, if the first usable time, which is the remaining usage time corresponding to the remaining level of the battery 109, is longer than the second usable time, which is the remaining usage time corresponding to the internal temperature of the ultrasonic probe 10, and if the difference between the first usable time and the second usable time is greater than or equal to the second difference, the drive determination function 3019 drives the cooler 107 with the cooling function of the strong level.

As such, by separating the intensity of the cooling function of the cooler 107, for instance, if the difference between the first usable time and the second usable time decreases by driving the cooler 107 with the power supplied from the battery 109, the intensity of the cooling function of the cooler 107 may be gradually weakened. Specifically, if the difference between the first usable time and the second usable time is long, by driving the cooler 107 with the cooling function of strong level and accordingly decreasing the difference of these, the cooler 107 may be driven with the cooling function of medium level and then of weak level. By this, the difference between the first usable time and the second usable time may be made as small as possible.

Likewise, if the difference between the first and the second usable times is small, it is also possible to adjust so that the first usable time becomes a value not too far apart from the second usable time by letting the drive determination function 3019 continuously drive the cooler 107 with the cooling function of weak level.

The cooler 107 having the plurality of different cooling functions may be realized by various cooling methods. For instance, if the cooler 107 is configured by the air-cooling device using a fan etc., the cooling function may be adjusted by modifying an rpm of the fan. Also, for instance, if the cooler 107 is configured by the liquid cooling device where the heat conducting fluid flows inside the pipe, the cooling function may be adjusted by modifying the flowing speed of the heat conducting fluid flowing inside the pipe. Further, for instance, if the cooler 107 is configured by a Piezo element, the cooling function may be adjusted by modifying the voltage applied to the Piezo element.

When driving the cooler 107 with the plurality of different intensities as such, at Step S19 in the cooling control function of FIG. 7, the drive determination function 3019 determines what intensity of the cooling function to drive the cooler 107 with when newly driving the inactive cooler 107, or if the cooler 107 is active, determines whether to modify the intensity of the cooling function or stop the drive.

Then, at Step S21, the drive determination function 3019 not only simply drives or stops the cooler 107, but also newly drives the cooler 107 with a designated intensity of the cooling function or modifies the cooling function of the active cooler 107 to the designated intensity based on the determination of the drive determination function 3019 at Step S19.

As described above, according to the ultrasonic diagnostic apparatus 1 of the present embodiment, the usable time of the ultrasonic probe 10 may be extended as possible by making the difference between the first usable time, which is the remaining usage time corresponding to the remaining level of the battery 109, and the second usable time, which is the remaining usage time corresponding to the internal temperature of the ultrasonic probe 10, as small as possible. By such, as conventionally, it becomes possible to keep the usable time of the ultrasonic probe 10 extended as possible while evading a performance of the ultrasonic probe 10 decreasing regardless of the operator's intention by automatically switching the ultrasonic probe 10 to a power savings mode.

In other words, by optimizing the relationship between the power consumption of the battery 109 and suppressing the internal temperature rise, it becomes possible to evade a situation of being unable to further use the ultrasonic probe 10 due to the internal temperature rise of the ultrasonic probe 10 even though the battery 109 still has remaining power. Also, in contrast, it becomes possible to evade a situation of being unable to further use the ultrasonic probe 10 due to the remaining level of the battery 109 being empty even though the internal temperature of the ultrasonic probe 10 is still in a usable range.

Modification of the First Embodiment

The ultrasonic probe 10 which the ultrasonic diagnostic apparatus 1 according to the first embodiment described above includes is based on a premise that the battery 109 is built in the ultrasonic probe 10 and cannot be easily detached. However, it is possible to have the battery 109 detachable from the ultrasonic probe 10 in the ultrasonic diagnostic apparatus 1 described above.

Figure 8:
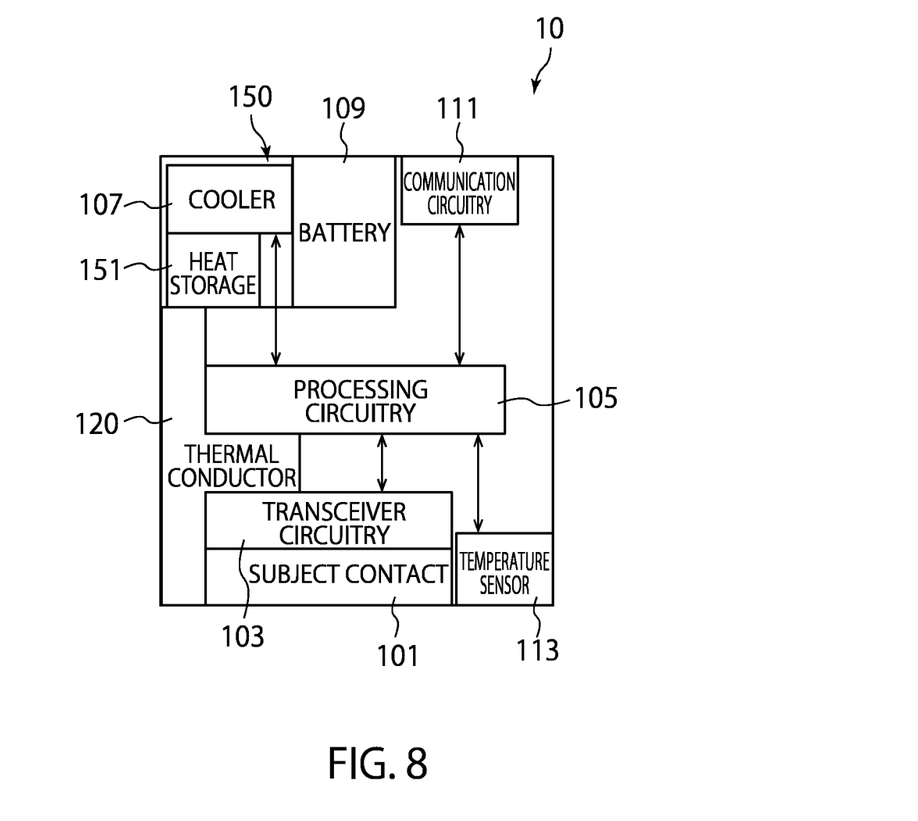
FIG. 8 is a diagram illustrating the internal layout of the ultrasonic probe describing a modified configuration of the ultrasonic probe.

FIG. 8 is a diagram illustrating the exemplary internal layout of the ultrasonic probe 10 where the battery 109 is incorporated to the battery pack 150 and made detachable from the ultrasonic probe 10, which corresponds to FIG. 3 described above. In a modification shown in FIG. 8, the battery pack 150 is detachable from the ultrasonic probe 10, and the operator may charge the battery 109 of the battery pack 150 with a charger by removing the battery pack 150 from the ultrasonic probe 10.

As shown in FIG. 8, the battery pack 150 has the cooler 107 and a heat storage 151 in addition to the battery 109. In other words, in the present modification, the cooler 107 is also incorporated into the battery pack 150 and drive controlled by the processing circuitry 301 in the apparatus body 30 via the processing circuitry 105. Then, the heat storage 151 is cooled by driving the cooler 107.

The heat storage 151 has a function of storing heat generated inside the ultrasonic probe 10. Thus, the usable time of the ultrasonic probe 10 may be extended by suppressing the internal temperature rise of the ultrasonic probe 10. For instance, the heat storage 151 is configured by a material which transits the phase from solid to liquid and absorbs (stores) latent heat when reaching a temperature higher than a predetermined phase transition temperature and transits the phase from liquid to solid and exhausts (dissipates) latent heat when reaching a temperature lower than the predetermined phase transition temperature. As a specific example, the heat storage 151 may be generated from materials such as organic substances such as wax and paraffin, inorganic hydrates such as sodium sulfate decahydrate and sodium acetate trihydrate, or low melting point metals such as wood metal and gallium.

In the present modification, the cooler 107 cools the heat storage 151. Then, when the battery pack 150 is removed from the ultrasonic probe 10 and charged, the heat storage 151 is cooled in parallel with the charge. By this, the stored heat of the heat storage 151 may be dissipated in a short amount of time, and the heat storage 151 may be sufficiently cooled when the battery 109 is completely charged.

As such, by arranging the battery 109, the cooler 107, and the heat storage 151 as the battery pack 150 detachable from the ultrasonic probe 10, a continuous usage time of the ultrasonic probe 10 may be extended. Also, the cooler 107 may efficiently suppress the internal temperature rise of the ultrasonic probe 10 by cooling the heat storage 151.

Second Embodiment

Although the ultrasonic diagnostic apparatus 1 according to the first embodiment described above drive controlled the cooler 107 provided on the ultrasonic probe 10 by the processing circuitry 301 of the apparatus body 30, the drive control of the cooler 107 may be performed by the processing circuitry 105 of the ultrasonic probe 10. In a second embodiment, an exemplary configuration where the processing circuitry 105 of the ultrasonic probe 10 controls the drive and stop of the cooler 107 will be described.

Figure 9:
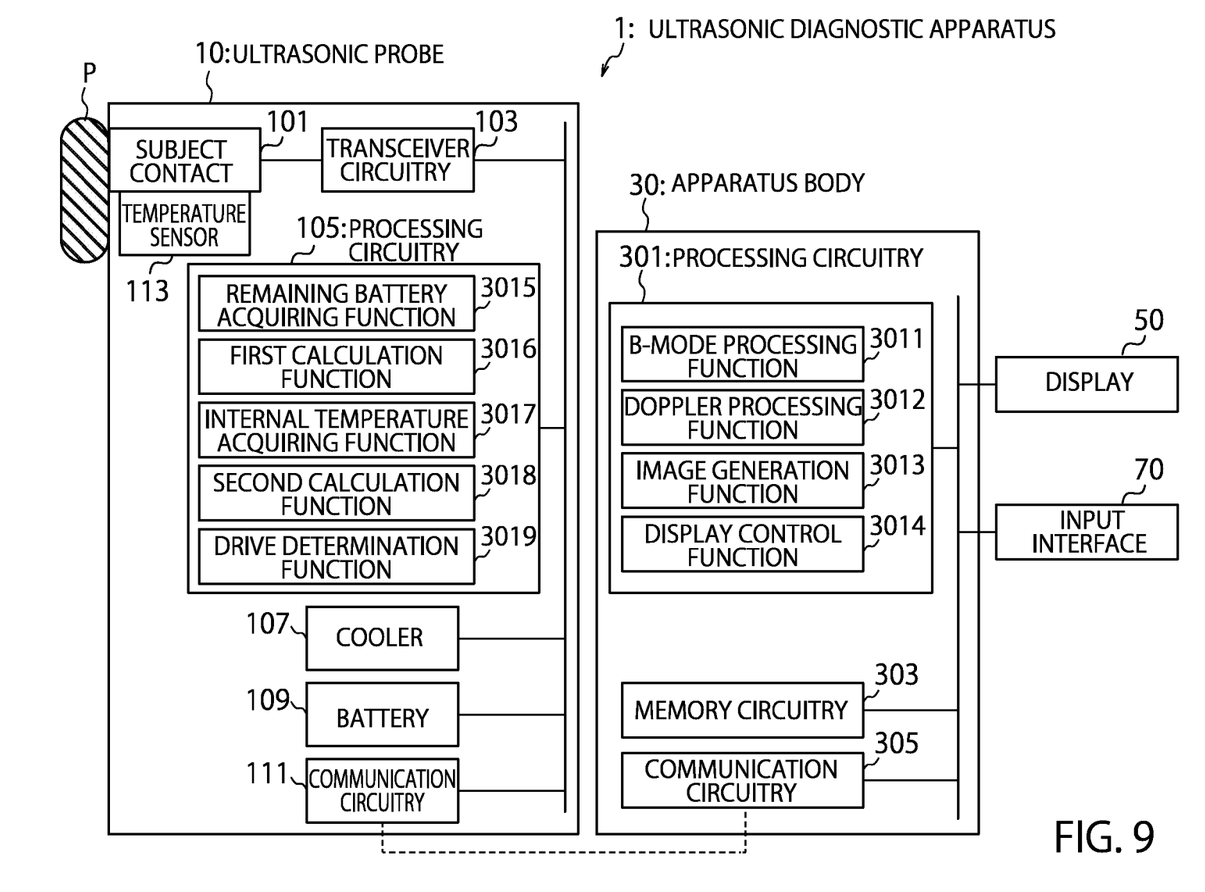
FIG. 9 is a block diagram illustrating the exemplary electrical configuration of the ultrasonic diagnostic apparatus according to a second embodiment.

FIG. 9 is a block diagram illustrating the exemplary electrical configuration of the ultrasonic diagnostic apparatus 1 according to the second embodiment, which corresponds to FIG. 2 of the first embodiment described above. As shown in FIG. 9, in the ultrasonic diagnostic apparatus 1 according to the present embodiment, the remaining battery acquiring function 3015, the first calculation function 3016, the internal temperature acquiring function 3017, the second calculation function 3018, and the drive determination function 3019 described in the first embodiment are provided in the processing circuitry 105 of the ultrasonic probe 10. For this reason, the processing circuitry 105 of the ultrasonic probe 10 configures the drive controller.

Roles and operations of the remaining battery acquiring function 3015, the first calculation function 3016, the internal temperature acquiring function 3017, the second calculation function 3018, and the drive determination function 3019 are equivalent to that of the first embodiment described above. Also, the cooling control process shown in FIG. 7 is executed by the processing circuitry 105 of the ultrasonic probe 10. However, there is no longer the need to intervene with the communication circuitry 305 and the communication circuitry 111 when the remaining battery acquiring function 3015 acquires the remaining level of the battery 109, and no longer the need to intervene with the communication circuitry 305 and the communication circuitry 111 when the internal temperature acquiring function 3017 acquires the internal temperature of the ultrasonic probe 10. In other words, the drive control of the independent cooler 107 is performed by the ultrasonic probe 10.

As such, even if the function of controlling the drive and stop of the cooler 107 is provided on the ultrasonic probe 10 based on the remaining level of the battery 109 and the internal temperature of the ultrasonic probe 10, the difference between the first usable time, which is the remaining usage time corresponding to the remaining level of the battery 109, and the second usable time, which is the remaining usage time corresponding to the internal temperature of the ultrasonic probe 10, may be made small as possible, extending the usable time of the ultrasonic probe 10 as long as possible.

Note that also in the second embodiment, equivalent to the modification shown in FIG. 8 in the first embodiment described above, the battery 109, the cooler 107, and the heat storage 151 may be configured as the battery pack 150 detachable from the ultrasonic probe 10. Then, by such, the continuous usage time of the ultrasonic probe 10 may be extended.

Note that the word "processor" used in above descriptions means circuits such as, for example, a Central Processing Unit (CPU), a Graphics Processing Unit (GPU), an Application Specific Integrated Circuitry (ASIC), a programmable logic device (for example, a Simple Programmable Logic Apparatus (SPLD), a Complex Programmable Logic Apparatus (CPLD), and a Field Programmable Gate Array (FPGA)). The processor executes functions by reading and executing programs stored in the memory. Note that programs may be configured to be directly integrated in the processor instead of being stored in the memory. In this case, the processor realizes functions by reading and executing programs stored in the circuitry. Note that the processor is not limited to the case arranged as a single processor circuitry, but may be configured as a single processor by combining a plurality of independent circuits to realize functions. Furthermore, a plurality of component elements may be integrated into one processor to realize the functions.

While certain embodiments have been described, these embodiments have been presented by way of example only and are not intended to limit the scope of the inventions. The novel devices and methods described in the present disclosure may be in a variety of other forms. Furthermore, various omissions, substitutions and changes may be made for the embodiments of the devices and method of described in the present disclosure without departing from the spirit of the inventions. The embodiments and their modifications are included in the scope and the subject matter of the invention, and at the same time included in the scope of the claimed inventions and their equivalents.

The invention claimed is:

1. An ultrasonic diagnostic apparatus, comprising:
   an ultrasonic probe configured to be connected to an apparatus body, the ultrasonic probe comprising a battery that supplies power to components of the ultrasonic probe and a cooler that cools inside the ultrasonic probe; and
   a drive controller configured to drive the cooler based on a remaining level of the battery and an internal temperature of the ultrasonic probe,
   wherein the ultrasonic probe further comprises
      a subject contact configured to contact a subject, send ultrasonic waves to the subject, and receive the ultrasonic waves from the subject, and
      a thermal conductor configured to be connected to conduct heat between the subject contact and the battery; and
   wherein the cooler cools the thermal conductor.

2. The ultrasonic diagnostic apparatus according to claim 1, wherein the drive controller is further configured to drive the cooler based on a first usable time and a second usable time, wherein the first usable time is a remaining usage time of the ultrasonic probe corresponding to the remaining level of the battery, and wherein the second usable time is a remaining usage time of the ultrasonic probe corresponding to the internal temperature of the ultrasonic probe.

3. The ultrasonic diagnostic apparatus according to claim 2, wherein the drive controller comprises processing circuitry configured to
   acquire the remaining level of the battery,
   calculate the first usable time based on the remaining level of the battery,
   acquire the internal temperature of the ultrasonic probe, and
   calculate the second usable time based on the acquired internal temperature.

4. The ultrasonic diagnostic apparatus according to claim 3, wherein the first usable time is a time until the remaining level of the battery drops below a first threshold, and the second usable time is a time until the internal temperature rises above a second threshold.

5. The ultrasonic diagnostic apparatus according to claim 2, wherein the drive controller comprises processing circuitry configured to drive the cooler when the first usable time is longer than the second usable time.

6. The ultrasonic diagnostic apparatus according to claim 5, wherein the processing circuitry is further configured to stop driving the cooler when the first usable time is shorter than the second usable time.

7. The ultrasonic diagnostic apparatus according to claim 2, wherein the drive controller is further configured to control the cooler to decrease a difference between the first usable time and the second usable time.

8. The ultrasonic diagnostic apparatus according to claim 1, wherein the battery is detachable from the ultrasonic probe.

9. The ultrasonic diagnostic apparatus according to claim 8, wherein the battery and a heat storage are configured as a battery pack detachable from the ultrasonic probe.

10. The ultrasonic diagnostic apparatus according to claim 9, wherein the cooler cools the heat storage.

11. The ultrasonic diagnostic apparatus according to claim 10, wherein the battery pack further comprises the cooler.

12. The ultrasonic diagnostic apparatus according to claim 1, wherein the ultrasonic probe is connected to the apparatus body with wireless communication, and
   wherein the cooler receives power from the battery.

13. An ultrasonic diagnostic apparatus comprising:
   an ultrasonic probe configured to be connected to an apparatus body, the ultrasonic probe comprising a battery that supplies power to components of the ultrasonic probe and a cooler that cools inside the ultrasonic probe; and
   a drive controller configured to drive the cooler based on a remaining level of the battery and an internal temperature of the ultrasonic probe, wherein the drive controller is configured to drive the cooler based on a first usable time and a second usable time, wherein the first usable time is a remaining usage time of the ultrasonic probe corresponding to the remaining level of the battery, and wherein the second usable time is a remaining usage time of the ultrasonic probe corresponding to the internal temperature of the ultrasonic probe,
   wherein the drive controller comprises processing circuitry and the processing circuitry is configured to drive the cooler when the first usable time is longer than the second usable time and to stop driving the cooler when the first usable time is shorter than the second usable time, and wherein the processing circuitry is further configured to drive a cooling function of the cooler with a different intensity in response to how great a difference between the first usable time and the second usable time is.

14. An ultrasonic probe used in an ultrasonic diagnostic apparatus, the ultrasonic probe comprising:

a battery configured to supply power to components of the ultrasonic probe;

a cooler configured to cool inside the ultrasonic probe;

a drive controller configured to drive the cooler based on a remaining level of the battery and an internal temperature of the ultrasonic probe;

a subject contact configured to contact a subject, send ultrasonic waves to the subject, and receive the ultrasonic waves from the subject; and a thermal conductor configured to be connected to conduct heat between the subject contact and the battery, wherein the cooler cools the thermal conductor.

15. The ultrasonic probe according to claim 14, wherein the drive controller is further configured to drive the cooler based on a first usable time and a second usable time, wherein the first usable time is a remaining usage time of the ultrasonic probe corresponding to the remaining level of the battery, and wherein the second usable time is a remaining usage time of the ultrasonic probe corresponding to the internal temperature of the ultrasonic probe.

16. The ultrasonic probe according to claim 15, wherein the drive controller comprises processing circuitry configured to:

acquire the remaining level of the battery;

calculate the first usable time based on the remaining level of the battery;

acquire the internal temperature of the ultrasonic probe; and calculate the second usable time based on the acquired internal temperature.

17. The ultrasonic probe according to claim 16, wherein the first usable time is a time until the remaining level of the battery drops below a first threshold, and the second usable time is a time until the internal temperature rises above a second threshold.

18. The ultrasonic probe according to claim 15, wherein the driver controller comprises processing circuitry configured to drive the cooler when the first usable time is longer than the second usable time.

19. The ultrasonic probe according to claim 18, wherein the processing circuitry is further configured to stop driving the cooler when the first usable time is shorter than the second usable time.

* * * * *